United States Patent [19]

Bradshaw et al.

[11] Patent Number: 4,996,277

[45] Date of Patent: Feb. 26, 1991

[54] NOVEL OLIGOETHYLENE OXIDE-CONTAINING ALKENES, ALKOXYSILANES, AND POLYSILOXANES

[76] Inventors: Jerald S. Bradshaw, 1616 Oaklane, Provo, Utah 84604; Milton L. Lee, 2400 N. 180 W., Pleasant Grove, Utah 84062; Karin E. Markides, 794 S. 700 East, Springville, Utah 84663

[21] Appl. No.: 153,369

[22] Filed: Feb. 8, 1988

[51] Int. Cl.$^5$ .............................................. C08G 77/06
[52] U.S. Cl. ........................................ 528/15; 528/23; 528/25; 528/42; 528/43; 556/450; 210/656; 570/126
[58] Field of Search ................... 556/450; 528/15, 23, 528/25, 43, 42

[56] References Cited

U.S. PATENT DOCUMENTS 4,745,169  5/1988  Sugiyama et al. .................. 556/450

OTHER PUBLICATIONS

O. O. Korhonen, "Glass Capillary Gas Chromatography of Chlorinated Methyl Acetates, Propanoates and Butanoates on Carbowax 20W and SE-30 Columns", Aug. 1982, vol. 15, #8, pp. 505-508.

J. R. Conder, et al., "Thermal Decomposition of Polyethlene Glycol 20M and Essential Oils in Gas-Liquid Chromatography and the Effect of Traces of Oxygen", Jun. 1983, Journal of Chromatography, 269, pp. 171-178.

Raymond D. Dandeneau, et al., "An Investigation of Glasses for Capillary Chromatography", Journal of High Resolution Chromatography & Chromatography Communications, vol. 12, Jun. 1979, pp. 351-356.

Paul H. Silvis, et al., "Applications of Bonded Carbowax Capillary GC Columns", American laboratory, Feb., 1987, pp. 41, 42, 44, 46, 47.

S. R. Lipsky et al., "Fused Silica Glass Capillary Columns for Gas Chromatographic Analyses", Journal of Chromatographic Science, vol. 18, Jan., 1980, pp. 1-9.

C. L. Woolley et al., "Deactivation of Small Diameter Fused Silica Capillary Columns with Organosilicon Hydrides", Journal of High Resolution Chromatography and Chromatography Communications, vol. 9, Sep., 1986, pp. 506-514.

Brian A. Jones, et al., "Contemporary Capillary Column Technology for Chromatography", Chromatography Forum, May-Jun., 1986, pp. 38-44.

Kohei Tamao et al., "Nickel-Phosphine Complex-Catalyzed Grignard Coupling I, Cross-Coupling of Alkyl, Aryl, and Alkenyl Grignard Reagents with Aryl and Alkenyl Halides: General Scope and Limitations", Bulletin or Chemical Society of Japan, vol. 49(7), 1976, pp. 1958-1969.

Jonathan D. Rich, "Silylative Decarbonylation: A New Route to Aromatic Chlorosilanes", General Electric Corporate Research & Development Center, A41, p. 44.

K. E. Markides et al., "Deactivation of Fused Silica Capillary Columns with Cyanopropylhydrosiloxanes"; Journal of High Resolution Chromatography & Chromatography Communications; 1985, vol. 8, pp. 741-748.

*Primary Examiner*—Melvyn I. Marquis

[57] ABSTRACT

Oligoethylene oxide-substituted aryl and aralkyl alkenes, oligoethylene oxide-substituted aryl and aralkyl alkoxy silanes and polysiloxane polymers containing oligoethylene oxide-substituted aryl and aralkyl sidechains and methods for their preparation are disclosed. The oligoethylene oxide-substituted aryl and aralkyl alkenes are used to prepare the oligoethylene oxide substituted polysiloxane polymers which are useful as stationary phase coatings in gas-liquid chromatography and supercritical fluid chromatography in the separation of various closely related chemical substances such as homologs and isomers. The oligoethylene oxide-substituted aryl and aralkyl alkoxy silanes are reactive towards silica particles for use as packing in liquid chromatography columns.

15 Claims, 5 Drawing Sheets

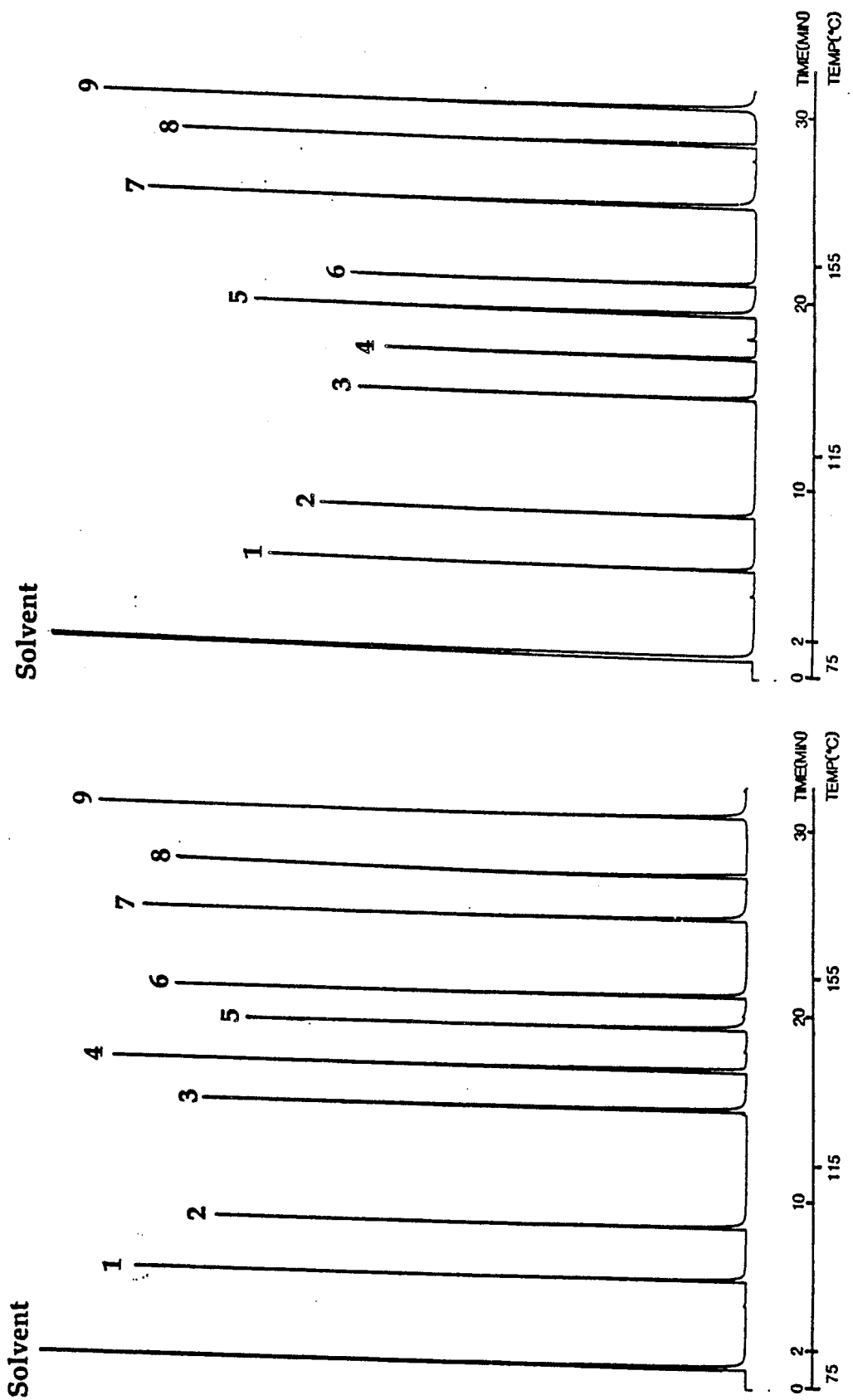

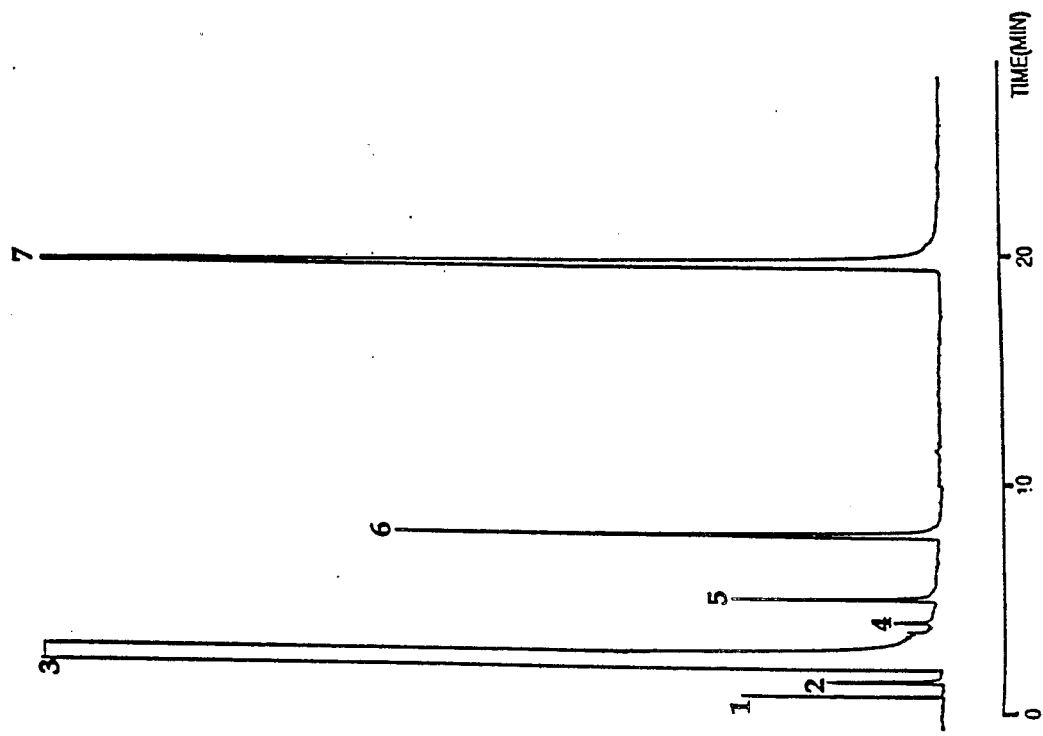
Fig. 2C
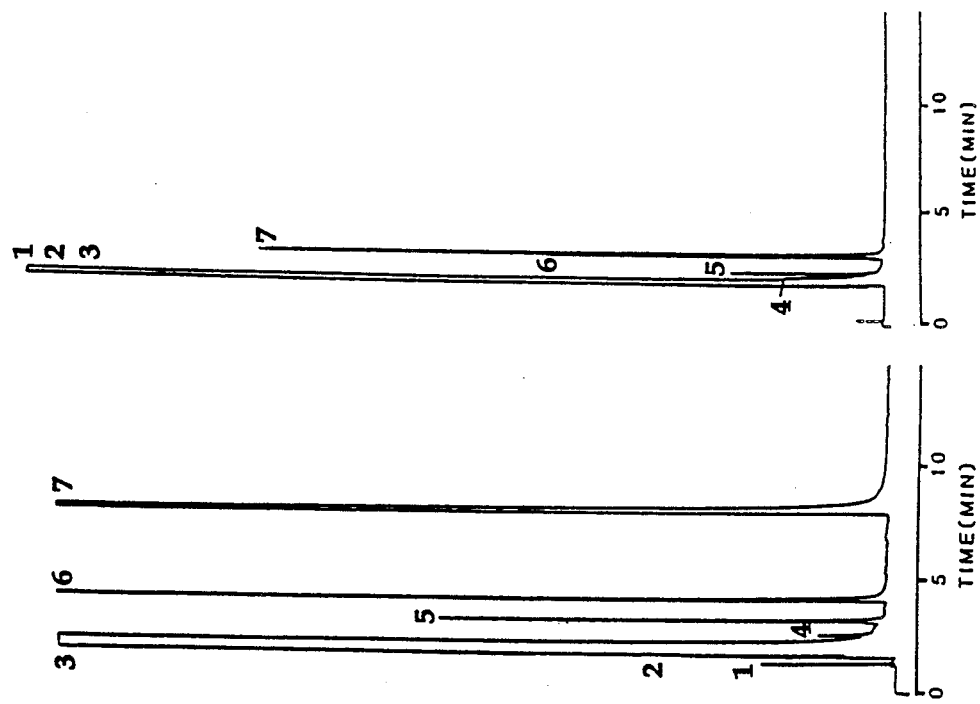
Fig. 2B
Fig. 2A

NOVEL OLIGOETHYLENE OXIDE-CONTAINING ALKENES, ALKOXYSILANES, AND POLYSILOXANES

1. FIELD OF THE INVENTION

The present invention relates to novel oligoethylene oxide-containing alkenes, alkoxy silanes, and polysiloxanes and the use of the polysiloxanes as stationary phases in gas-liquid and supercritical fluid chromatographic separations and analyses of various substances and the use of hydro-substituted oligoethylene oxide-containing polysiloxanes as well as alkoxy silanes to bind to silica particles for use in liquid chromatographic separations and analyses of various substances.

2. PRIOR ART

Polysiloxane gums have proven to be the most popular materials for stationary phases in both gas and supercritical fluid chromatography. These materials exhibit high thermal stabilities with regard to film rearrangement and chemical breakdown. The polysiloxanes have also demonstrated exceptionally high permeability to solutes giving high efficiencies in the separation of a variety of chemical mixtures. The methyl-substituted polysiloxanes (such as SE-30) are excellent stationary phases in that the order of elution is largely determined by the boiling points (vapor pressures) of the solutes in the mixture.

Many mixtures require a more polar or polarizable phase in order to obtain an efficient and selective separation. Polyethylene glycol (PEG phases) have been developed to allow solute separations based on polarity properties of the solute in addition to boiling point (or vapor pressure) properties of the solute. Carbowax 20M is a typical PEG phase which has wide popularity. By way of example, I. O. O. Korhonen in *GLASS CAPILLARY CHROMATOGRAPHY OF CHLORINATED METHYL ACETATES, PROPANOATES, AND BUTANOATES ON CARBOWAX AND SE-30 COLUMNS*, Chromatographia, 1982, Vol. 15, No. 8. 505-508, has shown that a mixture of 27 of the title compounds was effectively separated on a Carbowax 20M column, but the separation attempted on an SE-30 phase was not efficient.

Even though the PEG phases provide excellent separations for polar compounds, their use is limited by the material's low thermal stability (220° C.), high minimum operating temperature (60° C.) and poor phase stability which results in short column lifetimes. These limitations have been the subject of research for the past few years. The thermal decomposition limitation has been discussed by J. R. Conder, et al., in *THERMAL DECOMPOSITION OF POLYETHYLENE GLYCOL 20M AND ESSENTIAL OILS IN GAS-LIQUID CHROMATOGRAPHY AND THE EFFECTS OF TRACES OF OXYGEN*, J. Chromatogr., 1983, Vol. 269, 171-178. They reported that even though the maximum suggested operating temperature for a carbowax phase may be up to about 250° C., the practical limit is 220°-230° C.

The PEG phases have one additional disadvantage. Since the PEG phases cannot be immobilized on the columns, many supercritical fluids used in supercritical fluid chromatography strip the PEG phase coatings from the capillary columns. Thus, the polar PEG phases are generally not useful for capillary supercritical fluid chromatography.

Thus, it will be recognized that what is needed in the art is a chromatographic phase, or phases that are similar in polarity and selectively to the popular PEG phases, that have both lower and higher operating temperatures, and that can be immobilized on a capillary column so that fluids will not strip or wash the phase off the columns. Similar phases bound onto silica particles for liquid chromatography (LC) columns would also be an important addition to LC technology. Chromatographic phases having these novel properties and exhibiting separation properties like polar polyethylene glycol phases are disclosed and claimed in this present invention.

BRIEF SUMMARY AND OBJECTIVES OF THE INVENTION

The present invention relates to oligoethylene oxide-containing alkenes having the following general formula:

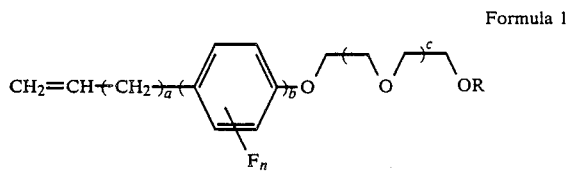

Formula 1

In the above Formula 1, a is an integer from 0 to about 12; b is an integer of 1 or 2 and c is an integer from 0 to about 10; R is hydrogen; alkyl of 1–22 carbon atoms; fluorinated alkyl of 1–22 carbon atoms, aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl;

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyridyl, pyrryl, nitro, cyano, chloro, bromo, fluoro, and $(OCH_2CH_2)_m-OR_9$ wherein m and n are integers of 1 to 4 and $R_9$ is methyl or ethyl.

The term aralkyl includes phenyl, thienyl, furyl, pyridyl and pyrryl substituted lower alkyl groups wherein "lower alkyl" means groups of about 1 to 8 carbon atoms As used herein the term "alkyl" refers to both straight and branched chain alkyl groups unless otherwise specifically noted. The term "perhaloalkyl" refers to perchloro-, perfluoro, and perbromo- substituted alkyl groups of 1 to 8 carbon atoms.

The present invention also relates to oligoethylene oxide-containing mono-, di-, or trialkoxysilanes having the following general formula:

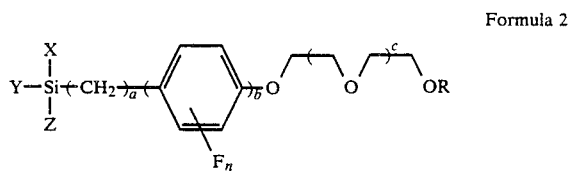

Formula 2

In the above Formula 2, a is an integer from 0 to about 14; b is an integer of 1 or 2 and c is an integer from 0 to about 10;

R is hydrogen; alkyl of 1-22 carbon atoms; fluorinated alkyl of 1-22 carbon atoms; aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl;

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyrryl, nitro, cyano, chloro, bromo, fluoro, and —$(OCH_2CH_2)_m$—$OR_9$ wherein m and n are integers of 1 to 4 and $R_9$ is methyl or ethyl;

X is methoxy or ethoxy and Y and Z are methoxy, ethoxy, methyl, ethyl or halogenated substituents thereof.

The present invention also relates to polymers comprising a polysiloxane backbone to which are attached the oligoethylene oxide-containing side chains formulated in accordance to Formula 1. Such polymers thus having the following general formula:

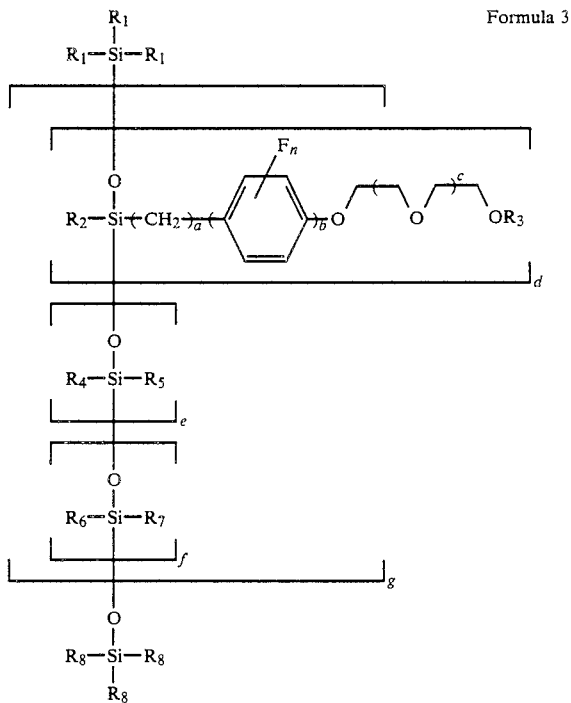

Formula 3

In the above Formula 3, a is an integer from 0 to about 14; b is an integer of 1 or 2; c is an integer from 0 to about 10; d is an integer from 1 to about 100; e is an integer from 0 to about 100; f is an integer from 0 to about 12; and g is an integer from 1 to about 50;

$R_1$ and $R_8$ are selected from the group consisting of lower alkyl, lower alkenyl, lower haloalkyl and phenyl;

$R_3$ is hydrogen; alkyl of 1-22 carbon atoms; fluorinated alkyl of 1-22 carbon atoms; aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl;

$R_2$, $R_4$, $R_5$ and $R_6$ are members selected from the group consisting of hydrogen, lower alkyl, phenyl, phenyl substituted lower alkyl, lower alkyl substituted phenyl, lower alkoxy substituted phenyl and halosubstituted phenyl;

$R_7$ is a member selected from the group consisting of alkyl of 1 to 12 carbon atoms, alkenyl of 2 to 8 carbon atoms, phenyl substituted lower alkyl and lower alkyl substituted phenyl. The essence of the $R_7$ group is that it is functional to react with a free radical source to facilitate crosslinking of two or more polysiloxane backbones;

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyrryl, nitro, cyano, chloro, bromo, fluoro, and —$(OCH_2CH_2)_mOR_9$ wherein m and n are integers of 1 to 4 and $R_9$ is methyl or ethyl.

Depending upon the starting materials, the polymer elements d, e, and f used to form the polymer chain will be ordered in a statistically governed sequence. The specific sequence of these polymer elements has little or no effect on the functionality of the polymer.

As noted in the above formula 3, the oligoethylene oxide of the present invention is attached to a polysiloxane backbone by a hydrocarbon linkage composed of oligomethylenylar or aryl groups depending upon the values of a and b. The polysiloxane backbone is crosslinked to one or more other polysiloxane chains to immobilize the material and provide higher thermal stability in gas chromatography and non-washout of the phase in polar supercritical fluid chromatography.

The oligoethylene oxide-containing alkene of Formula 1 is converted to a mono-, di-, or trialkoxysilane as shown in Formula 2, which alkoxysilane is reactive towards silica particles, thus, allowing the attachment of the oligoethylene oxide group to silica particles for use in liquid chromatography (LC) or SFC. It should be noted that the a values in Formulas 1 and 2 are not necessarily the same value.

Selectivity and capacity for polar solutes and inertness towards acids and alcohols has made polyalkylene glycol ether phases popular for use in gas chromatography. The polyethylene glycol ether phase (Carbowax 20M) was one of the first polar phases that could be successfully deposited on fused silica surfaces. Likewise, Carbowax deactivation became a popular and simple way of creating an "inert" surface on the fused silica capillary material for coating non-polar to medium-polar stationary phases as reported by R. D. Dandeneau et al., in *AN INVESTIGATION OF GLASSES FOR GAPILLARY CHROMATOGRAPHY*, J. High Resoln. Chromatogr./Chromatogr. Commun., 1979, Vol. 2, 351-355.

As previously mentioned, the usefulness of Carbowax 20M as a stationary phase is restricted due to its relatively low thermal stability, 220°-240° C.; high minimum operating temperature, 60° C.; and poor chemical stability (resulting in short column lifetimes). Attempts to improve Carbowax 20M, such as increasing the molecular weight (Superox.4) and the addition of crosslinking sites to immobilize the phase on the column wall (Bondable PEG, Stabilwax, etc.), have proven successful in extending the applicable temperature range slightly, with a maximum allowable operating temperature of 260°-280° C., and a minimum operating temperature of 20° C. as discussed by P. H. Silvis, et al., in *APPLICATIONS OF BONDED CARBOWAX CAPILLARY GC COLUMNS*, Amer. Lab., 1987, Vol. 19, 41–47. Despite the temperature constraints, Carbowax 20M is a widely used stationary phase in capillary chromatography because of its high coating efficiencies in fused silica columns and unique selectivity, which allows resolution of polar compounds having similar boiling points that cannot be separated using methyl silicone columns. It also represents the only commercially available polyethylene glycol ether stationary phase for fused silica capillary columns that has a carbon-oxygen backbone.

The thermal stabilities of Carbowax deactivated columns are a matter of controversy. Although claims have been made of temperature stabilities above 300° C., studies have shown that these columns are not stable for extended use beyond 250° C. as mentioned in the article by Conder, et al., given in the prior art section. In addition to thermal instability, polar polymer deactivation layers will also influence the polarity of the column. These effects are so pronounced that for fused-silica columns, the Carbowax deactivation method is no longer considered a viable form of deactivation for phases other than Carbowax as reported by S. R. Lipsky, et al., in *FUSED SILICA GLASS CAPILLARY COLUMNS FOR GAS CHROMATOGRAPHIC ANALYSES*, J. Chromatogr. Sci., 1980, Vol. 18, 1–9. Recently, effort has been placed on producing deactivation layers that are chemically compatible with the stationary phase and are thermally stable to above 300° C. as shown by C. L. Woolley, et al., *DEACTIVATION OF SMALL DIAMETER FUSED SILICA CAPILLARY COLUMNS WITH ORGANOSILICON HYDRIDES*, J. High Resoln. Chromatogr./Chromatogr. Commun., 1986, Vol. 9, 506–514.

The number of usable stationary phases is growing. Nearly all new phases are based on a polysiloxane backbone. Good diffusion properties for solutes in the stationary phase constitutes one of the conditions necessary for optimal performance in chromatography. It is well known that polysiloxane phases possess the best diffusion properties of the polymeric material known today. Substitution on the polysiloxane backbone has been diverse, depending on the chromatographic need. Stationary phases range from polar, cyanophenyl substituted, to non-polar, alkyl substituted polysiloxanes as reported in a review by B. A. Jones, et al., *CONTEMPORARY CAPILLARY COLUMN TECHNOLOGY FOR CHROMATOGRAPHY*, Chromatography Forum, 1986, Vol. 1, 38–44.

It is, therefore, an object of the present invention to provide novel oligoethylene oxide compounds and polymers.

It is also the objective of the present invention to provide new polysiloxane stationary phases with oligoethylene oxide substituents which are usable both at higher and lower temperatures than the PEG phases.

A further objective of the present invention is to provide a polysiloxane stationary phase with oligoethylene oxide substituents which can be immobilized for use in capillary supercritical fluid chromatography with polar mobile phases.

Another object of the present invention is to provide superior methods for separating various chemical compounds from mixtures thereof using gas-liquid chromatography.

A further object of the present invention is to provide stationary phases which are capable of performing separations based on the polarity properties of the solutes in addition to vapor pressure and other solute properties.

Yet another object of the present invention is to provide superior methods for separating various chemical compounds from mixtures thereof using supercritical fluid chromatography.

It is another object of the present invention to provide liquid chromatography packings containing the oligoethylene oxide materials.

Yet another object of the present invention is to provide superior methods for separating various chemical compounds from mixtures thereof using liquid chromatography.

These and other objects and features of the present invention will be more fully apparent from the following description and appended claims, taken in conjunction with the accompanying drawings.

BRIEF DESCRIPTION OF THE DRAWINGS

FIGS. 1A and 1B illustrate two gas-liquid chromatograms, wherein an alcohol-hydrocarbon mixture was separated. FIG. 1A represents a separation made using Carbowax 20M, a prior art stationary phase, while FIG. 1B represents a separation made using a stationary phase in accordance with one embodiment the present invention.

FIGS. 2A, 2B and 2C illustrate three gas-liquid chromatograms wherein a fusel oil mixture was separated. FIG. 2A represents a separation made at 40° C. column temperature using the same stationary phase as in FIG. 18, FIG. 2B represents a separation made using Carbowax 20M, a prior art stationary phase, and FIG. 2C represents a separation made at 20° C. column temperature using the same stationary phase as in FIG. 2A.

FIG. 3A represents a separation made using Carbowax 20M, a prior art stationary phase, while FIG. 3B represents a separation made using a stationary phase made in accordance with another embodiment of the present of invention.

DETAILED DESCRIPTION OF THE PREFERRED EMBODIMENTS

OLIGOETHYLENE OXIDE-SUBSTITUTED ALKENE EMBODIMENTS

Figure 3A:
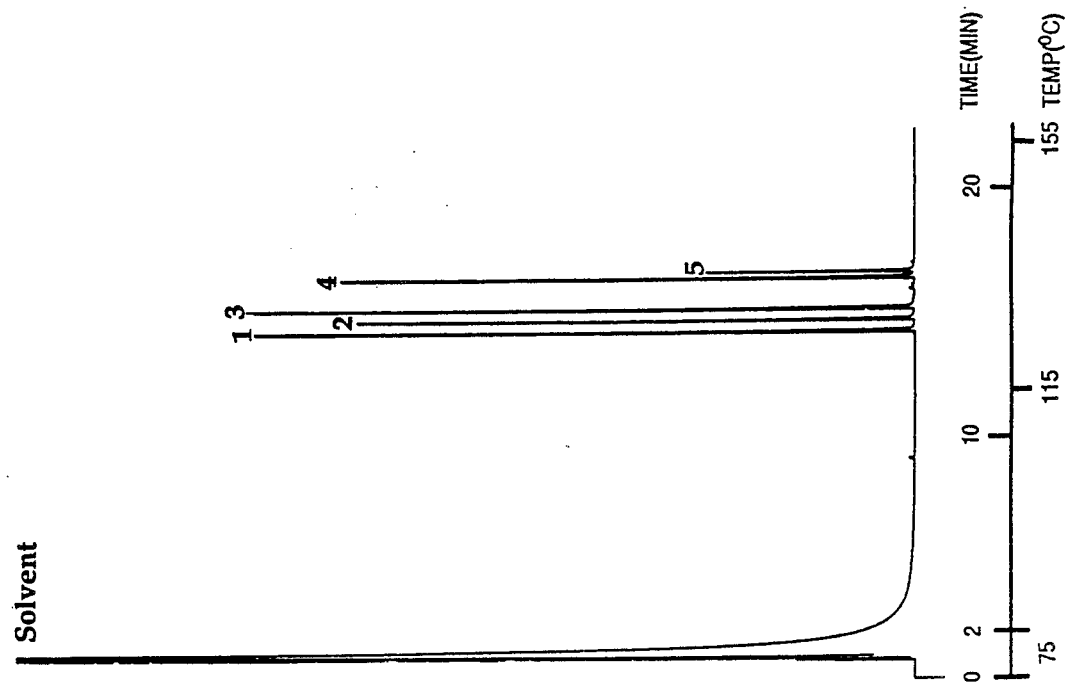
FIGS. 3A and 3B illustrate two gas-liquid chromatograms wherein five dimethylaniline isomers are separated.

The present invention relates to novel oligoethylene oxide-substituted alkenes, which are used to prepare the oligoethylene oxide-substituted alkoxysilanes and polymers. The oligoethylene oxide-containing alkenes of the present invention have the following general formula:

Formula 1

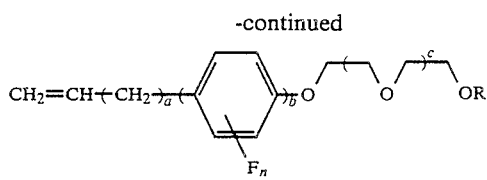

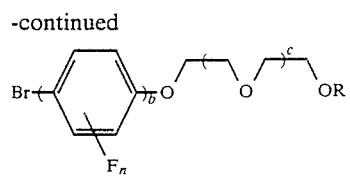

In Formula 1 above, a is an integer from 0 to about 12, with 1 being preferred; b is an integer of 1 or 2 with 1 being preferred; and c is an integer from 0 to about 10 with 1 to about 5 being preferred. In one particularly preferred embodiment a, b and c are all 1.

In Formula 1, R is hydrogen; alkyl of 1-22 carbon atoms; fluorinated alkyl of 1-22 carbon atoms; aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl. In particularly preferred embodiments R is methyl.

Also, in Formula 1, F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyrryl, nitro, cyano, chloro, bromo, fluoro, and —$(CH_2CH_2)_mOR_9$ wherein m and n are integers of 1 to 4 and $R_9$ is methyl or ethyl. In particularly preferred embodiments F is hydrogen or methoxy and n=1.

Thus, one particularly preferred compound has a=1; b=1; c=1; R=methyl, and F=H. A second particularly preferred compound has a=1; b=1; c=1; R=methyl; F=methoxy; and n=1.

Further, it will be recognized that substitutions of any of the foregoing chemical groups for R will be within the scope of this invention. By way of example only, substituting a halogen in one of these chemical groups would be considered to be within the scope of the present invention. Thus, all well known chemical substitutions or derivatives of the compounds of Formula 1 are to be considered within the scope of the present invention.

One presently preferred procedure in preparing compounds in accordance with Formula 1 where b=1 or 2 is given in Procedure I below.

PROCEDURE I

In this procedure, an excess of oligoethylene oxide tosylate is first reacted with p-bromophenol or 4-(p-bromophenyl)phenol as shown in Equation 1. In Equation 1, the oligoethylene oxide tosylate (or halide) and p-bromophenol react to form an oligoethylene oxide-substituted bromobenzene. As will be appreciated, the values of b, c and n and the nature of R and F in Equation 1 below will depend on the specific compound to be made.

Equation 1

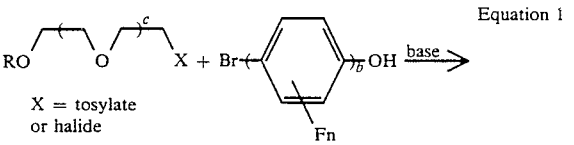

X = tosylate or halide

In order to achieve the reaction of Equation 1, the 4-bromophenol [or 4.(4-bromophenyl)phenol]is dissolved into solution at room temperature with a strong basic solution such as two or more equivalents of potassium hydroxide (KOH) or sodium hydroxide (NaOH) in an appropriate solvent such as a glyme or ethanol. Next, the oligoethylene oxide tosylate (or halide) is dripped, for example, via an addition funnel, into the stirring 4-bromophenol solution over a one to three hour period of time, while the solution is at room temperature. The resulting mixture may be refluxed under a condenser at a temperature corresponding to the reflux temperature of the mixture. If the oligoethylene oxide tosylate (or halide) is not a liquid at room temperature, it may be dissolved in an appropriate solvent such as glyme or ethanol before addition, or the solid itself may be slowly added to the mixture. Completion of the reaction may require refluxing of the mixture for a period of about six to twenty-four hours.

The resultant oligoethylene oxide-substituted bromobenzene solution is cooled to about 20° C. and the product is isolated from the refluxed solution by extraction with a suitable solvent such as ether. The organic layer (such as ether) is washed first with aqueous base such as 1 M sodium hydroxide (NaOH) and then with water until the water was neutral. The resulting organic layer is dried over a drying agent such as anhydrous magnesium sulfate. The drying agent is filtered and the organic solvent is removed under vacuum. The resulting product is distilled under vacuum if it is a liquid or recrystallized if it is a solid. The solid is dissolved in an appropriate heated solvent, such as ethanol or hexane, and then cooled to achieve recrystallization.

The next step in Procedure I is to react the purified oligoethylene oxide-substituted bromobenzene with magnesium and then with the appropriate alkenyl bromide in order to produce the oligoethylene oxide-containing alkene corresponding to the compounds of Formula 1 as shown in Equation 2 below.

Equation 2

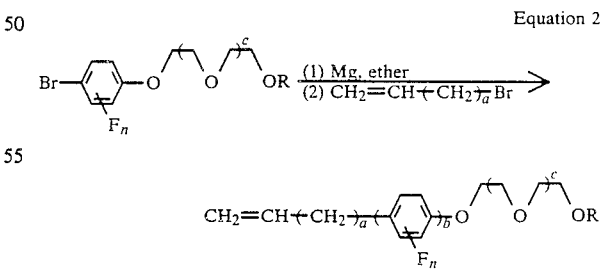

To achieve the reaction of Equation 2, an equivalent of magnesium turnings is added to ethyl ether or tetrahydrofuran (THF) in a dry 3-necked flask. The mixture is stirred and refluxed for a short time and an equivalent of the oligoethylene oxide-substituted bromobanzene in ethyl ether or THF is dripped into the mixture over a two or three hour period. The reaction between the oligoethylene oxide-substituted bromobenzene and magnesium may have to be initiated by adding a small amount of iodine or 1,2-dibromoethane. An atmosphere of inert gas, such as argon, is kept over the reaction mixture. After the bromide is added, the mixture is refluxed an additional 10 to 20 hours. The mixture is then cooled to −78° C. using a dry ice-acetone bath. A mixture of about 0.8 equivalents of alkenyl bromide in benzene (about 1 part of alkenyl bromide to 2 parts of benzene) is slowly added and the mixture was stirred at −78° C. and allowed to slowly warm to room temperature. A nickel. phosphine complex catalyst can be used for alkenyl halides that are less reactive towards Grignard reagents. This catalyst system is reported by K. Tamao, et al., in *NICKEL-PHOSPHINE COMPLEX CATALYZED GRIGNARD COUPLING. I. CROSS-COUPLING OF ALKYL. ARYL. AND ALKENYL HALIDES: GENERAL SCOPE AND LIMITATIONS*, Bull. Chem. Soc. Japan, Vol. 49, 1958–1969 (1976). The mixture is then refluxed under a reflux condenser for 10–20 hours. The reaction mixture is then cooled and extracted with a suitable solvent such as ether. The organic layer is washed once with dilute aqueous hydrochloric acid, then once with brine (saturated aqueous sodium chloride) and then with water until the water wash is neutral. The organic layer is dried over a suitable drying agent such as anhydrous magnesium sulfate. The drying agent is filtered and the organic solvent is evaporated under vacuum. The resulting alkane corresponding to Formula 1 (where $b=1$ or 2) is distilled if it is a liquid, or recrystallized from a suitable solvent if it is a solid.

It is understood that compounds corresponding to Formula 1 ($b=1$ or 2) can also be prepared from any 4-alkenylphenol (such as eugenol) and the appropriate oligoethylene oxide tosylate (or halide) as shown in Equation 3 below.

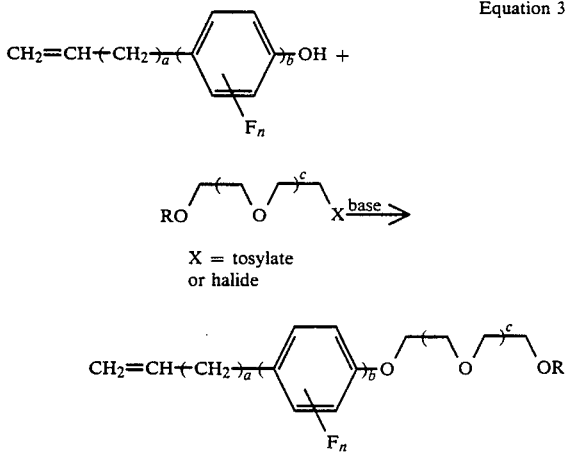

Equation 3

X = tosylate or halide

In this case, the reaction would be carried out as discussed above for Equation 1 except that 4-alkenylphenyl [or 4-(4-alkenylphenyl)phenol] would be used instead of 4-bromophenol [or 4-(4-bromophenyl)phenol]. Eugenol (4-allyl-2-methoxyphenol) is a good starting material for this reaction and gives the 3-(4-oligooxaalkyl-3-methoxyphenyl) 1-propene compound (the compound of Equation 3 where F is a methoxy group).

The following examples are given to illustrate compounds which have been made in accordance with Formula 1 of the present invention. These examples are illustrative only, and are not comprehensive of the many different compounds which have been or can be made within the scope of this invention.

EXAMPLE 1

In this example an oligoethylene oxide-substituted alkene was made wherein $a=1$, $b=1$, $c=1$, and R=methyl (-CH$_3$) and F=hydrogen in Formula 1.

First, 4-[2-(2-methoxyethox)ethoxy]bromobenzene was prepared. In this regard, 21.6 g (0.125 mol) of 4 bromophenol and 5 g of sodium hydroxide were stirred overnight in 100 mL of glyme. The mixture was then heated at reflux for 2 hours to dissolve the remaining sodium hydroxide. This solution was cooled and 6.2 g (0.0226 mol) of 2-(2-methoxyethoxy)ethyl tosylate (prepared by reacting the monomethyl ether of diethylene glycol with tosyl chloride) was added at once. The resulting mixture was stirred at room temperature (4 hours), then heated to reflux overnight. It was then cooled and extracted with 300 mL of ethyl ether. The ethyl ether layer was washed first with aqueous 2N potassium hydroxide and then with saturated aqueous brine until the aqueous layer was neutral. The ethyl ether solution was dried over anhydrous magnesium sulfate and evaporated under vacuum to give 5.23 g of an oil. The oil was distilled to give 3.26 g (72%) of 4-[2-(2-methoxyethoxy)ethoxy]bromobenzene, bp 103°–112° C./O. 1mm; NMR(($\delta$):3.40 (3H,s), 3.50–3.92 (6H,m), 4.12 (2H,M), 6.80 (2H,d), 7.36 (2H,d).

Magnesium turnings (0.83g, 0.032 mol) and 10 mL of anhydrous tetrahydrofuran (THF) were placed in a dry 3-necked round bottom flask. The mixture was stirred under reflux in an argon atmosphere for about 20 minutes. The previously prepared 4-[2-(2-methoxyethoxy)ethoxy]bromobenzene (7-0g, 0.025 mol) in 30 mL of anhydrous THF was slowly dripped into the stirring magnesium mixture. A small amount (about 0.1 mL) of 1,2-dibromoethane was initially added to start the Grignard reaction. After the bromide was added, the mixture was refluxed overnight under an argon atmosphere. The mixture was then cooled to −78° C. and 15 mL (0.17 mol) of allyl bromide in 30 mL of spectral grade benzene was added. The resulting mixture was stirred and allowed to slowly warm to room temperature and then refluxed overnight. The mixture was cooled and exacted with ethyl ether. The ethyl ether layer was washed with aqueous 3N hydrochloric acid, aqueous saturated brine and then with water until the organic layer was neutral. The ethyl ether solution was dried over anhydrous magnesium sulfate and the solvent was removed. The product was distilled to give 2.78 g (47%) of the desired 3-(4-[2-(2-methoxyethoxy)ethoxy]phenyl]-1-propene, bp 105°–113° C./0.2mm; NMR($\delta$): 3.30(2H,d), 3.36(3H,s), 3.46–3.92(6H,m), 4.12(2H,m), 5.00(2H,m), 5.95(1H,m), 6.80(2H,d), 7.04(2H,d).

EXAMPLE 2

In this example, an oligoethylene oxide-substituted alkene was made wherein $a=1$, $b=1$, $c=1$, R=methyl (-CH$_3$), F=methoxy (-OCH$_3$), and $n=1$ in Formula 1.

Potassium metal (6.15 g) and 150 mL of t-butyl alcohol were mixed together in a 1,3-necked round bottom flask. The solution was heated slightly and stirred until all of the potassium had reacted. The solution was kept under an atmosphere of Argon at all times. A dripping funnel was used to add 25.40 g of eugenol (4-allyl-2-methoxyphenol). The solution turned solid as the phenoxide was formed, and it was dissolved in approximately 150 mL of dimethylformamide (DMF). A mixture of 41.16 g of 2-(2-methoxyethoxy)ethyl tosylate and about 350 mL of DMF was added by dripping funnel to the flask containing the eugenol and base. The solution was heated to between 40°-50° C. and allowed to stir for several days. The reaction was monitored by TLC, using a 95:5 benzene:methanol solvent system. The disappearance of the tosylate and eugenol reactants indicated that the reaction was proceeding. The reaction was stopped when the eugenol was reacted. The 500 mL solution was added to a 2 L separating funnel along with 300 mL of ethyl ether and 400 mL of distilled water. The ether layer was drained after mixing, and the water layer was washed with another 300 mL portion of ethyl ether. The combined ethyl ether phases were washed with 300 mL of 2.7 M KOH to remove any alcohol. Distilled water was used to wash the ethyl ether layer until it was neutral. The ethyl ether solution was dried over anhydrous magnesium sulfate and then the ether was removed under reduced pressure. Approximately 29.86 g of crude product was obtained. The product was slightly viscous, yellow oil. This oil was distilled to give 5.9 g of product, bp 135° C./0.30 mm; NMR9 ($\delta$): 3.35(2H, d), 3,44(3H, s), 3.66(6H, m) 3.84(3H, s), 4.20(2H, t), 5.0(1H, m), 5.16(1H, m), 5.95(1H, m), 6.80(3H, m).

OLIGOETHYLENE OXIDE-SUBSTITUTED ALKOXYSILANE EMBODIMENTS

The present invention also relates to novel oligoethylene oxide-containing mono-, di-, or trialkoxysilanes which exhibit utility for the preparation of polymers used for deactivation of fused silica columns or for the coating of silica particles which are used in columns for liquid chromatography (LC) and supercritical fluid chromatography (SFC). These new oligoethylene oxide-containing mono-, di-, or trialkoxysilanes also can be used to directly coat silica particles with an oligoethylene oxide-containing material which coated particles will also be useful in LC or SFG columns. The novel oligoethylene oxide-containing compounds of this embodiment have the following general formula.

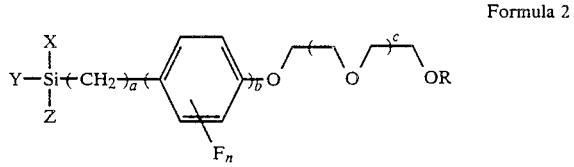

Formula 2

In the above Formula 2, a is an integer from 0 to about 14, with 0 and 3 being preferred; b is an integer of 1 or 2, with 1 being preferred; and c is an integer form 0 to about 10 with 1 to about 5 being preferred.

R is hydrogen, alkyl of 1-22 carbon atoms; fluorinated alkyl of 1-22 carbon atoms; aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl. In particularly preferred embodiment R is methyl;

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyrryl, nitro, cyano, chloro, bromo, fluoro, and —$(CH_2CH_2)_m$-$OR_9$ wherein m and n are integers of 1 to 4 and $R_9$ is methyl or ethyl. In particularly preferred embodiment R is hydrogen;

X is methoxy or ethoxy and Y and Z are methoxy, ethoxy, methyl, ethyl or halogenated substituents thereof A particularly preferred embodiment is when X and Y are ethoxy and Z is methyl.

In accordance with the above, one preferred compound has a=3; b=1; c ±1; R=ethyl; F=H; X and Y=ethoxy and Z=methyl. Another preferred compound has a=0; b=1, c=1; R=ethyl; F=H; R=methyl; X and Y=methoxy; and Z=methyl.

It is to be understood that if X, Y and Z all are ethoxy that the compound of Formula 2 will be a triethoxysilane. Likewise, a diethoxysilane would have X and Y as ethoxy groups and Z would be an alkyl or aryl group. One preferred embodiment has X and Y as ethoxy (—$OCH_2CH_3$) groups and Z as a methyl (—$CH_3$) group.

One presently preferred procedure for preparing compounds in accordance with Formula 2 is given in Procedure II below.

PROCEDURE II

In this procedure, a mixture of oligoethylene oxide-containing alkenes (prepared as shown in Procedure I) is reacted with a hydrosilane containing 1 to 3 alkoxy groups in an approximate 1.2 to 1 molar ratio, in accordance to Equation 4.

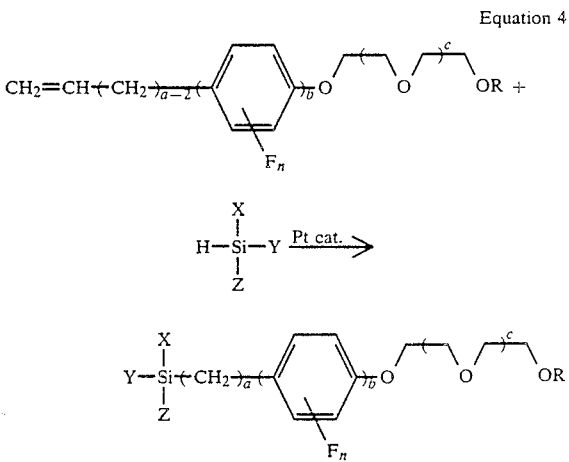

Equation 4

In order to achieve the reaction of Equation 4, a mixture of the oligoethylene oxide-containing alkene (prepared as described in Procedure I), the hydrosilane (H-SiXYZ) and benzene are stirred at a temperature of between 70° C. and 90° C. for about 2 hr under an inert gas, such as argon, in a flask containing a reflux condenser. A small amount of chloroplatinic acid is added and the mixture is refluxed for a period of between 10 hours and 24 hours. The product oligoethylene oxide-containing mono-, di-, or trialkoxysilane is purified usually by distillation. If the product is a solid, it can be purified by recrystallization using an appropriate non proton-containing solvent such as benzene or hexane.

The oligoethylene oxide-containing mono-, di-, or trialkoxysilane compound in Formula 2 can also be prepared by the reaction of an oligoethylene oxide-containing alkyl (or arylalkyl) halide and magnesium followed by reaction with a tetra-, tri-, or dialkoxysilane.

The following example is given to illustrate one compound which has been made in accordance with Formula 2. This example is exemplary only, and is not comprehensive of the many different compounds that have been or can be made in accordance with this embodiment of the invention.

EXAMPLE 3

In this example, an oligoethylene oxide-containing compound is prepared wherein $a=3$, $b=1$, $c=1$, $R=$ethyl ($-CH_2CH_3$), $F=$hydrogen, X and $Y=$ethoxy ($-OCH_2CH_3$) and $Z=$methyl ($-CH_3$) in Formula 2.

This compound was made by first heating a mixture of 2.8 g (0.011 mol) of 3-{4-[2-(2-ethoxyethoxy)ethoxy]-phenyl}-1-propene (prepared as in Example 1), 5 g of benzene and 1.1 equivalent of methyldiethoxysilane under an argon atmosphere at 85° C. for one hour. After one hour, a trace amount (0.01 μL) of 1 part chloroplatinic acid in 1 part ethanol and 98 parts THF was added and the mixture was heated overnight at 85° C. The product was isolated by distillation to give 4.2 g (97%) of methyl diethoxy 3-{4-[2-(2-ethoxyethoxy)ethoxy]-phenyl}propysilane, bp 135° C./0.08mm; NMR (δ): 0.20(3H,s), 0.65(2H,m), 1.05(9H,t), 1.50(2H,m), 2.70(2H,t), 3.90(12H,m), 7.0(2H,d), 7.15(2H,d).

OLIGOETHYLENE OXIDE-SUBSTITUTED POLYSILOXANE POLYMER EMBODIMENTS

The present invention also relates to novel polymers containing oligoethylene oxide units which are formed either by attaching the oligoethylene oxide-substituted alkenes of Formula 1 to a polysiloxane backbone or by hydrolyzing and polymerizing the dialkoxy oligoethylene oxide-substituted silanes of Formula 2 to form polymers having the following general formula.

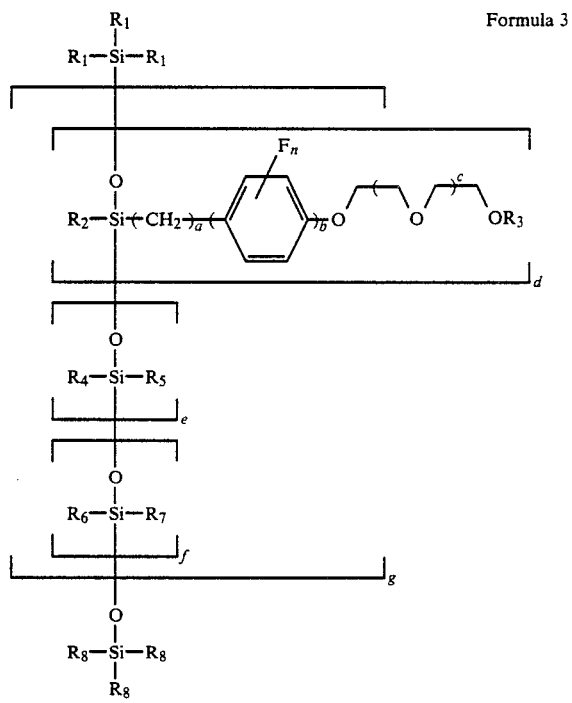

Formula 3

In the above Formula 3, a is an integer from 0 to about 14, with 3 being preferred; b is an integer of 1 or 2, with 1 being preferred; and, c is an integer from 0 to about 10, with 1 to about 5 being preferred. Although it is possible for c to be 0 or greater than 5, a short ethylene oxide chain would have too few ether groups leading to lower polarity and extra long ethylene oxide chains could lead to diminished stability of the polysiloxane backbone. In a particularly preferred embodiment $a=3$, $b=1$ and $c=1$.

$R_1$ and $R_8$ are selected from the group consisting of lower alkyl, lower alkenyl, lower haloalkyl and phenyl. The $R_1$ groups attached to the silyl atom may be the same or different as may the $R_8$ groups. Moreover, $R_1$ and $R_8$ may be different. In a particularly preferred embodiment all $R_1$ and $R_8$ groups are methyl, i.e. forming trimethylsilyl groups.

$R_3$ is hydrogen; alkyl of 1-22 carbon atoms; fluorinated alkyl of 1-22 carbon atoms; aryl selected form the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamido, lower dialkylamino and lower perhaloalkyl substituents thereof; and lower aralkyl. In particularly preferred embodiments $R_3$ is methyl.

$R_2$, $R_4$, $R_5$ and $R_6$ are members selected from the group consisting of hydrogen, lower alkyl, phenyl, phenyl substituted lower alkyl, lower alkyl substituted phenyl, lower alkyoxy substituted phenyl and halosubstituted phenyl. In a particularly preferred embodiment $R_2$, $R_4$, $R_5$ and $R_6$ are all methyl groups.

$R_7$ is a member selected from the group consisting of alkyl of 1 to 22 carbon atoms, alkenyl of 2 to 8 carbon atoms, phenyl substituted lower alkyl and lower alkyl substituted phenyl. As stated above, the essence of the $R_7$ group is that it must be functional to react with a free radical source to facilitate crosslinking of two or more polysiloxane backbones. Specific illustrations of $R_7$ groups are vinyl, octyl and p-tolyl.

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, thienyl, furyl, pyridyl, pyrryl, nitro, cyano, chloro, bromo, fluoro, and $-(OCH_2CH_2)_m-OR_9$ wherein m and n are integers of 1 to 4 and $R_9$ is methyl or ethyl. In two preferred embodiments F is hydrogen or methoxy.

In Formula 3, d is an integer from 1 to about 100; e is an integer from 0 to about 100; f is an integer from 0 to about 12; and g is an integer from 1 to about 50. As stated above, depending upon the starting materials, the polymer elements d, e, and f used to form the polymer chain will be ordered in a statistically governed sequence. The specific sequence of these polymer elements has little or no effect on the functionality of the polymer. However, the percentages of d, e, and f in Formula 3 determine the percentage of oligoethylene oxide units on the polysiloxane chain. Thus, if e is 0 and f is only 0.5 to 2% of d, the polysiloxane chain will have nearly 50% of the oligoethylene oxide groups. Compared to the numbers of d, f is normally very small. In one presently preferred embodiment polymers made in accordance with Formula 3 have a d value of about 1 to about 100, and an e value of 0.

Further, the degree of crosslinking during the formation of the polymer relates to the f values. In the most preferred embodiment of the present invention, polymers made in accordance with Formula 3 have an f value which is about 4% of the combined values of d and e.

The value of g in Formula 3 determines the degree of polymerization and thus the number of oligoethylene oxide units in the polymer. In one presently preferred embodiment, g is about 5.

In the most preferred embodiments, polymers made in accordance with Formula 3 will have a g value within the range of 1 to about 50 with values of between about 2 to 50 being particularly preferred. However, it will be appreciated that the precise value of g will depend on the particular application involved, with the optimum value of g depending on such factors as the desired efficiency and solubility of the resulting polysiloxane.

One compound embodied within the scope of Formula 3 has $a=3$; $b=1$; $c=1$; $d=97$; $e=0$; $f=$ about 3; $g=$ about 4; $R_1$ and $R_8=$ methyl; $R_2$, $R_4$, $R_5$ and $R_6=$ methyl; $R_7=$ octyl or ethyl groups; and $F=H$. In a second compound $a=3$; $b=1$; $c=2$; $d=50$; $e=50$; $f=$ about 3; $g=$ about 4; $R_1$ and $R_8=$ methyl; $R_2$, $R_4$, $R_5$ and $R_6=$ methyl; $R_7=$ octyl or ethyl groups and $F=$ methoxy and $n=1$. In a third compound $a=0$; $b=1$; $c=2$; $d=100$; $e=0$; $f=$ about 3; $g=$ about 3–5; $R_1$ and $R_8=$ methyl; $R_2$, $R_4$, $R_5$ and $R_6=$ methyl; $R_7=$ octyl and $F=H$. In a fourth compound $a=3$; $b=1$; $c=1$; $d=6$; $e=6$; $f=0$; $g=$ about 1; $R_1$ and $R_8=$ methyl; $R_2$, $R_4=$ methyl; $R_3=$ ethyl; $R_5=H$ and $F=H$.

The preferred procedures to prepare the polymers in accordance with Formula 3 are given in Procedures III and IV below.

PROCEDURE III

In this procedure, the appropriate polyhydromethylsiloxane is first prepared. The polyhydromethylsiloxane itself is not part of this invention. The polysiloxane containing the oligoethylene oxide function is part of the invention and is best made by reacting the oligoethylene oxide-containing alkene in Procedure I with a polyhydromethylsiloxane. The preparation of the polyhydromethylsiloxane is here reported. In this regard, the appropriate mixture of 1,3,5,7-tetramethylcyclotetrasiloxane (D'4) and octamethylcyclotetrasiloxane (D4) along with a trace amount of hexamethyldisiloxane (to effect endcapping) are treated with an appropriate acid such as trifluoromethane sulfonic acid for about 4 days at room temperature. It is to be recognized that the relative amounts of D'4 and D4 will determine the final ratio of d and e in the compounds of Formula 3. If the polymer made in accordance to Formula 3 needs to have about 50% of the oligoethylene oxide side group, then no D4 is used and e will be 0. It is also recognized that where equimolar amounts of D'4 and D4 are used, the values of d and e in the final polymers made in accordance with Formula 3 will be approximately equal. After the above mixture of D'4, D4, hexamethyldisiloxane and acid are reacted, the mixture is neutralized using an appropriate base such as sodium bicarbonate. The resulting polymer is dissolved in a minimum amount of $CH_2Cl_2$ (usually about 10 mL per gram of polymer) and precipitated with methanol (usually one to three times the amount of ($CH_2Cl_2$). The mixture is centrifuged, the solvents are decanted and the precipitate is again dissolved in $CH_2Cl_2$. This process of dissolution in $CH_2Cl_2$ and precipitation with methanol is repeated 3 or 4 more times. The resulting polymer is dried under reduced pressure before being used in the next step.

In the second step of Procedure III, the oligoethylene oxide-substituted alkenes prepared in Procedure I above are attached to the polyhydro. methylsiloxane made in the first step of Procedure III. The alkene of Procedure I is purified to remove any alcohol or carbonyl functions by passing it through activated charcoal and alumina using a purified non-alcoholic solvent such as benzene as eluant. The thus purified alkene within the scope of Formula 1 and the polymer are mixed with the reactants being combined with about 1.1 to 1.5 equivalents of the alkene for each Si-H in the polymer. Small amounts (usually about 2 or 3% of the combined values of d and e in Formula 3) of 1-octene can also be added to the mixture. Only small amounts of 1-octene are needed for crosslinking purposes. To the mixture of these reactants is added enough benzene or toluene to dissolve the reactants and a catalytic amount of chloroplatinic acid (about 0.03 M) in 1 part ethanol and 98 parts THF. The resulting mixture is heated to a temperature range of about 75° C. to about 90° C. for a period of about 2 hours to about 24 hours until the reaction is completed. Ethylene may be bubbled through the mixture to insure that all the Si-H groups have been reacted.

The polymer thus produced is precipitated by adding an equal volume of methanol to the reaction mixture. The polymer is then purified by dissolving it in a minimal amount of $CH_2Cl_2$ and subsequently precipitating it with methanol. This process may be repeated two or more times in order to obtain better purity. The purified product is then dried at a temperature within a range of 30° C. to about 60° C. under a vacuum of 0.1 to 1 torr for a period of 12 to 24 hours.

The following examples are given to illustrate various polymers which have been made or may be made in accordance with Formula 3 of the present invention. Again, these examples are illustrative only, and are not comprehensive of the many different polymers which can be made in accordance with this embodiment.

EXAMPLE 4

In this example, a polysiloxane gum within the scope of Formula 3 was made wherein $a=3$, $b=1$, $c=1$, $d=97$, $e=0$, $f=$ about 3, $g=$ about 4, $R_1$ and $R_8=$ methyl, $R_2$, $R_3$, $R_4$, $R_5$, and $R_6=CH_3$, $R_7=$ octyl or ethyl groups and $F=$ hydrogen.

In this regard, a 50% hydro-containing polyhydromethylsiloxane was prepared by stirring a mixture of 2.63 g of 1,3,5,7-tetramethylcyclotetrasiloxane (D'4), 0.029 g of hexamethyldisiloxane, and 5 mg of trifluoromethane sulfonic acid for 50 hours at room temperature. The mixture was neutralized with 30 mg of hexamethyldisilazane while being stirred for 5 min. The resulting polymer (MW about 25,000) was dissolved in 10 mL of $CH_2Cl_2$, the polymer was precipitated by adding 30 mL of methanol, the mixture was centrifuged, and the solvents were decanted. The polymer was again dissolved in $CH_2Cl_2$ and precipitated by methanol for a total of four more times. The polymer was then dried for 10 hours under reduced pressure.

In the second step of Example 4, the polyethylene oxide-containing alkene of Example 1 was attached to the polymer. The alkene was purified by passing it through an activated charcoal column followed by a neutral alumina column using spectral grade benzene as the eluant. The thus purified 3-{4-[2-(2-ethoxyethoxy)ethoxy]phenyl}-1propene of Example 1 (0.75 g, 3.2 mol), about 0.3 mmol of 1-octene, 0.15g (2.5 mmol) of the 25,000 MW polyhydromethylsiloxane containing 50% Si-H as reported above and 1.5 mL of spectral grade benzene were mixed and heated to 90° C. over a 1 hour period in a Teflon vial under an argon atmosphere.

Chloroplatinic acid (11 μL of a solution of 1 part H$_2$PtCl$_6$.6H$_2$O, 1 part ethanol and 98 parts tetrahydrofuran) was then added to the mixture. The reaction was nearly complete in 2 hours as measured by the remaining Si-H band in the IR. Ethylene was then bubbled through the mixture to react with all the residual Si-H units. The vial was then capped and the temperature was held at 90° C. for 16 hours. The solvents were removed and the gummy product was dissolved in 2 mL of methylene chloride and precipitated with 5 mL of methanol and 5 mL of water. The material was centrifuged and the solvents were decanted. The process of dissolution in methylene chloride and precipitation with methanol was repeated two more times. The product 0.26g (35%), a light gray gum, was dried overnight in a vacuum oven. The NMR spectrum of the gum exhibited the proper ratio for the Si-(CH$_3$ peaks at δ 0.18 versus the aromatic peaks at δ 6.78(d) and 6.98(d) for about 50% of the polyethylene oxide substituent. Since 1-octene was added initially and ethylene was used to remove the last traces of Si-H, it is estimated that there is about 48% of the oligoethylene oxide substituent in this polymer.

EXAMPLE 5

In this example, a polysiloxane gum within the scope of Formula 3 was made wherein a=3, b=1, c=2, d=50, e=50, f=about 3, g=about 4, R$_1$ and R$_8$=methyl, R$_2$, R$_3$, R$_4$, R$_5$, and R$_6$ =methyl, R$_7$=any combination of octyl or ethyl groups, F=methoxy, and n=1.

The oligoethylene oxide-containing alkene of Example 2 was attached to the 25,000 molecular weight, 50% hydro-containing polymer of Example 4. Approximately 1% of 1-octene was added for cross-linking purposes. A weight of 0.44 g of the polymer and 2.91 g of the alkene (purified by washing through charcoal) (1.5 molar excess) were added to a 50 mL Teflon centrifuge tube and dissolved in benzene. The final total volume of alkene, polymer and benzene was approximately 10 mL. The mixture was heated to 85° C. and stirred under an atmosphere of argon for 1 hour. After one hour, the catalyst, 0.4% of H$_2$PtCl$_6$, was added at a concentration of 15 ppm. The volume of catalyst used came to 37 μL. An IR spectrum was taken just before the catalyst was added, and then the reaction was monitored by IR. The reaction was complete when the Si-H peak at 2340 cm$^1$ was mostly gone. A small amount of 1-octene was added to completely react the remaining Si-H. Benzene was added as needed. The solution was a clear yellow. When the reaction was complete, the polymer was precipitated with methanol and water. The solution was centrifuged to separate the polymer and solvent. Excess methanol was evaporated in an oven until the polymer was as dry as possible. The remaining solvent was removed by a vacuum oven and low heat for at least 12 hours.

The polymer (2.68 g) was a light brown and extremely viscous liquid, but not a gum. The NMR spectrum of the phase gave the proper ratio of Si-CH$_3$ peaks versus the O—CH$_3$ peak for about 50% of the polyethylene oxide substituent.

PROCEDURE IV

In this procedure, a mixture of the diethoxymethylsilane containing the desired polyethylene oxide unit of Formula 2, dimethoxydimethylsilane (if needed), and about 2% of either dimethoxymethyloctylsilane or dimethoxymethylvinylsilane is hydrolyzed with water and polymerized at temperatures of 40° C. to 115° C. using tetramethylammonium hydroxide as a catalyst. The resulting polymer is end-capped using chlorodimethylvinylsilane or trimethylsilyl chloride. Even though the dimethoxysilanes are used to form the polymers, dichlorosilanes may also be used.

The starting oligoethylene oxide-substituted dimethoxysilane compounds used in Procedure IV are prepared in Procedure II or are prepared using the reactions shown in Equation 5 below.

Equation 5

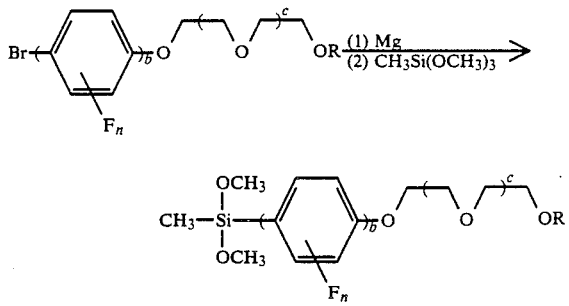

The 4-bromophenyl-(or 4-bromobiphenyl)-substituted oligoethylene oxide needed to prepare the dimethoxysilane material in Equation 5 is prepared as shown in Equation 1 of Procedure I. The phenyl substituted silanes can also be prepared by reacting a polyethylene oxide-substituted benzoyl chloride with 1,1,2,2-tetrachloro-1,2-dimethyldisilane using a palladium catalyst as was recently reported by J. D. Rich, *SILYLATIVE DECARBOXYLATION: A NEW ROUTE TO AROMATIC CHLOROSILANES*, 1987, Abstract of the Eighth International Symposium on Organosilicon Chemistry, St. Louis, Mo., June 7-12, 1987. The chlorosilanes, thus obtained by the Rich process, are readily converted to methoxysilanes by treatment with trimethyl orthoformate.

The following examples utilizing Procedure IV are given to illustrate polymers which have been made in accordance with Formula 3. As above, these are given by way of example only, and are not comprehensive of the many different polymers which have been and can be made in accordance with the procedures taught.

EXAMPLE 6

In this example, a polysiloxane gum of Formula 3 was made wherein a=0, b=1, c=2, d=100, e=0, f=about 3, g=3.5, R$_1$, and R$_8$=methyl, R$_2$, R$_3$, R$_4$, R$_5$ and R$_6$=methyl, R$_7$=octyl groups and F=H.

In this regard, the dimethoxy methyl 4-(1,4,7,10-tetraoxandecyl)phenyl silane of Formula 2 wherein a=0, b=1, c=2, F=H, R=methyl (-CH$_3$), X and Y=methoxy(—OCH$_3$) and Z=methyl was first prepared using the Example 1 procedure by reacting 9.65 g (0.03 mol) of 4-(1,4,7,10-tetraoxaundecyl)bromobenzene with 0.85 g of magnesium in 20 mL of dry THF under an argon atmosphere while stirring. When nearly all of the magnesium had reacted, the mixture was cooled to −78° C. and 12.36 g (0.09 mol) of trimethoxymethylsilane was added at once. The mixture was allowed to slowly warm to room temperature and was stirred for 60 hours. About 100 mL of hexane was added and the magnesium salts were filtered. The product (about 45% yield) was a clear oil after the solvents were evaporated under vacuum.

In the second step, 0.5 g of dimethoxy methyl 4-(1,4,7,10-tetraoxaundecyl)phenylsilane synthesized above and 10 μL of diethoxymethylvinylsilane were hydrolyzed in 10 mL of a 1 to 1 mixture of acetonitrile and water over a 16 hour period. The solvents were then removed under vacuum and the hydrolyzed material was dissolved in 3 mL of benzene. Five drops of 10% (w/w) of tetramethylammonium hydroxide in methanol were added to the mixture. The resulting mixture was heated under an argon sparge in a Teflon vial from 40° C. to 115° C. at 0.5° C. per minute. The 115° C. temperature was maintained for an additional 30 minutes. The solvents were evaporated during this 30-minute period. The remaining material became a gum when cooled to room temperature. The gum was dissolved in 3 ml of benzene and a small amount of chlorodimethylvinylsilane was added. The resulting solution was stirred for 16 hours to effect endcapping. The polymer was then precipitated with 2 mL of a 50:50 mixture of methanol and water. The mixture was centrifuged and the solvents were decanted. The polymer was dissolved in 2 mL of methylene chloride, precipitated with 2 mL of the methanol-water mixture, centrifuged, and the solvents again decanted. This process of dissolution and precipitation was repeated two more times and then the polymer was dissolved in 2 mL of methylene chloride and filtered through a Teflon filter. The solvent was evaporated and the gummy material (0.2 g) was dried under vacuum.

EXAMPLE 7

In this example, an oligosiloxane fluid of Formula 3 was made wherein $a=3$; $b=1$; $c=1$; $d=6$; $e=6$; $f=0$; $g=$about 1; $F=$hydrogen; $R_1$ and $R_8$ =trimethylsilyl; $R_2$ and $R_4=$methyl, $R_3=$ethyl; $R_5=$hydrogen; and $R_6$ and $R_7$ are not present since $f=0$.

This oligomer was prepared by combining 4.2 g of the compound of Example 3 with 0.66 g of 1,3,5,7-tetramethylcyclotetrasiloxane (D'4) and 100 mg of Amberlyst 15 (a polymer bound organosulfonic acid) in a Teflon vial. This mixture was stirred under an argon atmosphere at room temperature for 2 days. After that time, 0.2 g of hexamethyldisilazane was added to terminate the reaction. The reaction mixture was filtered and the solvents were removed under reduced pressure. The product was dried under reduced pressure for 16 hours to give 3.5 g (70%) of the low molecular weight oligomer.

UTILITY

The polymers of the present invention have shown utility in connection with stationary phases used in gas-liquid and supercritical fluid chromatography. One presently preferred procedure for applying the polymers of the present invention to a chromatographic column is given in Procedure V below.

PROCEDURE V

In this procedure, the polymer to serve as the stationary phase is statically coated on fused silica capillary columns. The fused silica capillaries (for example, about 10-30 meters long and about 50-500 micrometers in inner diameter) are prepared for chromatographic analysis in accordance with the present invention as follows.

First, the fused silica capillaries are purged with dry nitrogen gas at about 250° C. for about two hours before use. The polymer is dissolved in methylene chloride or other low boiling solvent at about 35° C. at a sufficient concentration to provide a film thickness of about 0.05-10 micrometers by the static coating method. Before filling the fused silica capillaries, the coating solution is carefully filtered through a two-micrometer metal filter device. The columns are then coated with the polymer and the columns are purged with nitrogen gas for about 30 minutes to remove all traces of solvent. The coating or stationary phase thus applied to the fused silica capillaries is next preferably crosslinked using azo-t-butane as free radical initiator.

To achieve such crosslinking, the coated columns are purged with azo-t-butane saturated nitrogen gas. The column ends are then sealed, and the columns are heated from about 40° C. to about 220° C. by increasing the temperature at the rate of about 4° C. per minute, and holding at the final temperature of about 220° C. for about 30-40 minutes. After crosslinking, the column is purged with dry nitrogen gas at room temperature to remove excess azo-t-butane and reaction by-products. Such a crosslinking procedure provides crosslinkages between the methyl, ethyl, octyl and/or methylene functional groups in the polymer. Of course, it will be recognized that other free radical initiators can be used instead of azo-t-butane and that the crosslinking reaction can be performed statically in a sealed column as set forth in this procedure, or dynamically where the column is purged with an inert gas during the reaction.

The following examples are given to illustrate the various silica columns for gas-liquid and supercritical fluid chromatography and silica particles for liquid chromatography which can be coated with materials made in accordance with Formula 3 of the present invention. These examples are exemplary only, and are not comprehensive of the many different coatings that can be made in accordance with the present invention.

EXAMPLE 8

In this example, the polymer of Example 4 was applied as a stationary phase in a gas-liquid chromatographic column. A fused silica capillary column, about 20 meters long and about 0.2 millimeters in inner diameter (supplied by Polymicro Technologies, Phoenix, Arizona) was deactivated at 300° C. using a cyanopropylhydrosiloxane procedure as described by K. E. Markides, et al., *DEACTIVATION OF FUSED SILICA CAPILLARY COLUMNS WITH CYANOPROPYLHYDROSILOXANES*, J. High Resolun. Chromatogr./Chromatogr. Commun., 1985, Vol. 8, 741-747. This deactivated silica column was statically coated with about a 0.15 micrometer film of the polymer of Example 1 as follows:

About 12 mg of this polymer was dissolved in about 5 mL of methylene chloride at about 35° C. Before filling the fused silica capillary, the polymer-containing solution was carefully filtered through a two-micrometer pore metal filter device. The capillary column was then coated with the polymeric solution to provide a film thickness of about 0.15 micrometers on the inside of the capillary column. The column was then purged with nitrogen gas for about 30 minutes to remove all traces of solvent.

The polymer thus applied to the fused silica capillary, was next crosslinked using azo-t-butane. To achieve this, the polymer-coated column was purged with azo-t-butane saturated nitrogen gas. The column ends were then sealed, and the column was heated from about 40°

C. to about 220° C. by increasing the temperature at a rate of about 4° C. per minute, and holding at the final temperature of about 220° C. for about 30-40 minutes. After the crosslinking procedure was completed, the capillary column was purged with dry nitrogen gas at room temperature to remove excess azo-t-butane and reaction by-products.

EXAMPLE 9

In this Example, the polymer of Example 5 was applied as a stationary phase to a gas-liquid chromatographic column in accordance with the procedure of Example 8.

ration achieved when the polymers of the present invention are used as stationary phases as compared to separations using the PEG phases. In each of the gas-liquid chromatograms illustrated in FIGS. 1-4, a Carlo Erba 5160 Mega Series gas chromatograph equipped with a flame ionization detector and a flame photometric detector was used. Hydrogen gas at 50-100 cm s$^{-1}$ was used as the carrier gas.

Table I lists the chromatographic properties of the new polymer phase of Example 4 as compared to both the commercially available PEG (Carbowax 20M) and the bondable PEG phase.

TABLE I

| Chromatographic Properties of Columns Coated with Polymer Phase of Example 4, Bondable PEG and Carbowax 20M Stationary Phases | | | | | | |
|---|---|---|---|---|---|---|
| Stationary phase | $C_{12}OH$* | | Biphenyl* | | Efficiency (Plates/m) | Operating Temp. Range (°C.) |
| | k' | RI | k' | RI | | |
| Example 4 | 16.0 | 1800 | 15.2 | 1920 | 5700 | 20 to 280 |
| Carbowax 20M | 11.4 | 1756 | 15.5 | 1925 | 5400 | 60 to 220 |
| Bondable PEG | 17.1 | 1985 | 14.2 | 1740 | 5600 | 40 to 260 |

*Column temperature = 120° C.

EXAMPLE 10

In this example, the polymer of Example 4 was applied as a stationary phase in a supercritical fluid capillary column. A fused silica column about 20 meters long and about 0.05 millimeters in inner diameter (supplied by Polymicro Technologies, Phoenix, Arizona) was statically coated with about 0.15 micrometer film of the polymer as in Example 8 except that the column was not deactivated before the polymer was applied.

EXAMPLE II

In this example, the oligosiloxane fluid of Example 7 in chloroform was mixed with silica gel particles in a ratio of 1 part fluid of Example 7 to 10 parts silica gel. The chloroform solvent was removed under vacuum on a rotary evaporator to insure a reasonably uniform coating of the fluid of Example 7 on the silica gel. The gel was then heated at 250° C. for 10 to 20 hours. The resulting material was suitable for use as an LC packing.

A similar type of packing can be prepared by coating the compound of Example 3 on silica gel and heating the resulting gel to effect a chemical bond.

Crosslinking of the polymeric stationary phase within the column helps to prevent washout of the polymer after repeated use. Additionally, the stationary phases of the present invention can be used in supercritical fluid chromatography where even higher demands are put on the crosslinked polymers. Such crosslinked polymers have been found to withstand the strong solubilizing properties of supercritical fluids. Thus, the present invention has also found utility in supercritical fluid chromatography applications.

The polymer coated columns of each of Examples 8 and 9 have been chromatographically tested for gas-liquid chromatography and have shown utility in separating various organic mixtures. The separation performance of the polymer phases of the present invention were compared with the performance of Carbowax 20M, the standard polyethylene glycol (PEG) polymer used for chromatographic separations and a new bondable polyethylene glycol phase supplied by Chromtech, Cromwell, CT.

In FIGS. 1-4 of the present application, several gas-liquid chromatograms are illustrated showing the sepa- In Table I, k' is the relative retention of the compound as compared to an unretained material such as methane gas and RI is the retention index which is based on the retention of the compound as compared to the retention of the normal-alkanes For example, a compound with an RI of 1850 elutes halfway between the retention times of $C_{18}$ and $C_{19}$ normal hydrocarbons. The data in Table I shows that there are no appreciable differences in the interaction with a neutral polarizable solute of the Example 4 phase and the PEG (Carbowax 20M) phase, but a noticeable difference in the operational temperatures does occur. Specifically, the Example 4 phase is usable from 20° C. to 280° C, while the Carbowax 20M phase is usable from 60° C. to 220° C. The Bondable PEG phase does show a noticeable increase in retention of the alcohol solute indicating that this phase is more polar than the other phases. Thus, it is clear that separations on the new oligoethylene oxide-containing polysiloxane phases of the present invention, such as illustrated by Example 4, are comparable to those of PEG and, more importantly, the new phases of this invention are usable at both lower temperatures and higher temperatures than the PEG (Carbowax) phases.

The fact that the new polyethylene oxide phases of this invention provide comparable separations of organic mixtures is also shown by a comparison of the separation of a hydrocarbon-alcohol mixture on the phase of Example 4 (B) and Carbowax 20M (A). The two chromatograms are shown as FIGS. 1B and 1A respectively. In FIGS. 1A and 1B, the peak identifications are as follows: (1) 2-octanol, (2) 1-octanol, (3) 1-decanol, (4) hexadecane, (5) 1,6-hexanediol, (6) 1-dodecanol, (7) 1,8-octanediol, (8) eicosane, and (9) 1,10-decanediol. As is shown in FIGS. 1A and 1B the retention and separation of the alcohol-hydrocarbon mixture by the phase of Example 4 are nearly the same as that by the Carbowax 20M phase.

The fact that the new polyethylene oxide-containing polysiloxane phases of the present invention are usable at lower temperatures than the PEG (Carbowax) phases is shown by a comparison of the separation of fusel oil. FIG. 2A represents a chromatogram made at 40° C. column temperature using the phase of Example 4, FIG. 2B represents a chromatogram made at 40° C. using Carbowax 20M, and FIG. 2C represents a chromatogram made at 20° C. using the phase of Example 4. FIGS. 2A, 2B and 2C show that phases of the present invention are usable at lower temperatures than the Carbowax phases. FIGS. 2A and 2C respectively show that the phase of Example 4 (Example 8 column) easily separates the fusel oil mixture at 40° C. and 20° C., while Carbowax 20M provides very poor separation at 40° C.

In FIGS. 2A, 2B and 2C as shown in FIG. 2B the peak identifications are as follows: (1) acetaldehyde, (2) methanol, (3) ethanol, (4) ethyl acetate, (5) 1-propanol, (6) isobutyl alcohol, and (7) isoamyl alcohol.

Figure 3B:
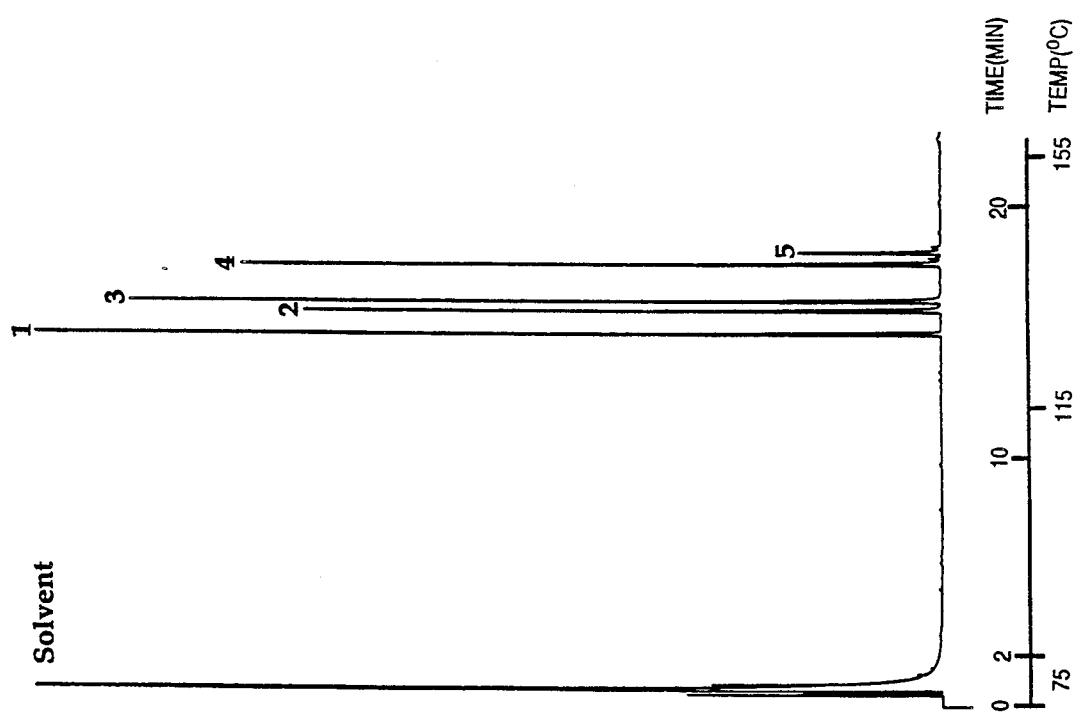

FIGS. 3A and 3B show gas chromatograms of the separation of various dimethylanilines by the new phase of Example 5 (Example 9 column) (FIG. 3B) as compared with the separation of this mixture with a Carbowax 20M column (FIG. 3A). As shown in FIGS. 3A and 3B, the separation of the mixture using the new phase of Example 5 is nearly the same as the separation using Carbowax 20M. In FIGS. 3A and 3B the peak identifications are as follows: (1) 2,6-dimethylaniline, (2) 2,5-dimethylaniline, (3) 3,5-dimethylaniline, (4) 2,3-dimethylaniline, and (5) 3,4-dimethylaniline.

Figure 4:
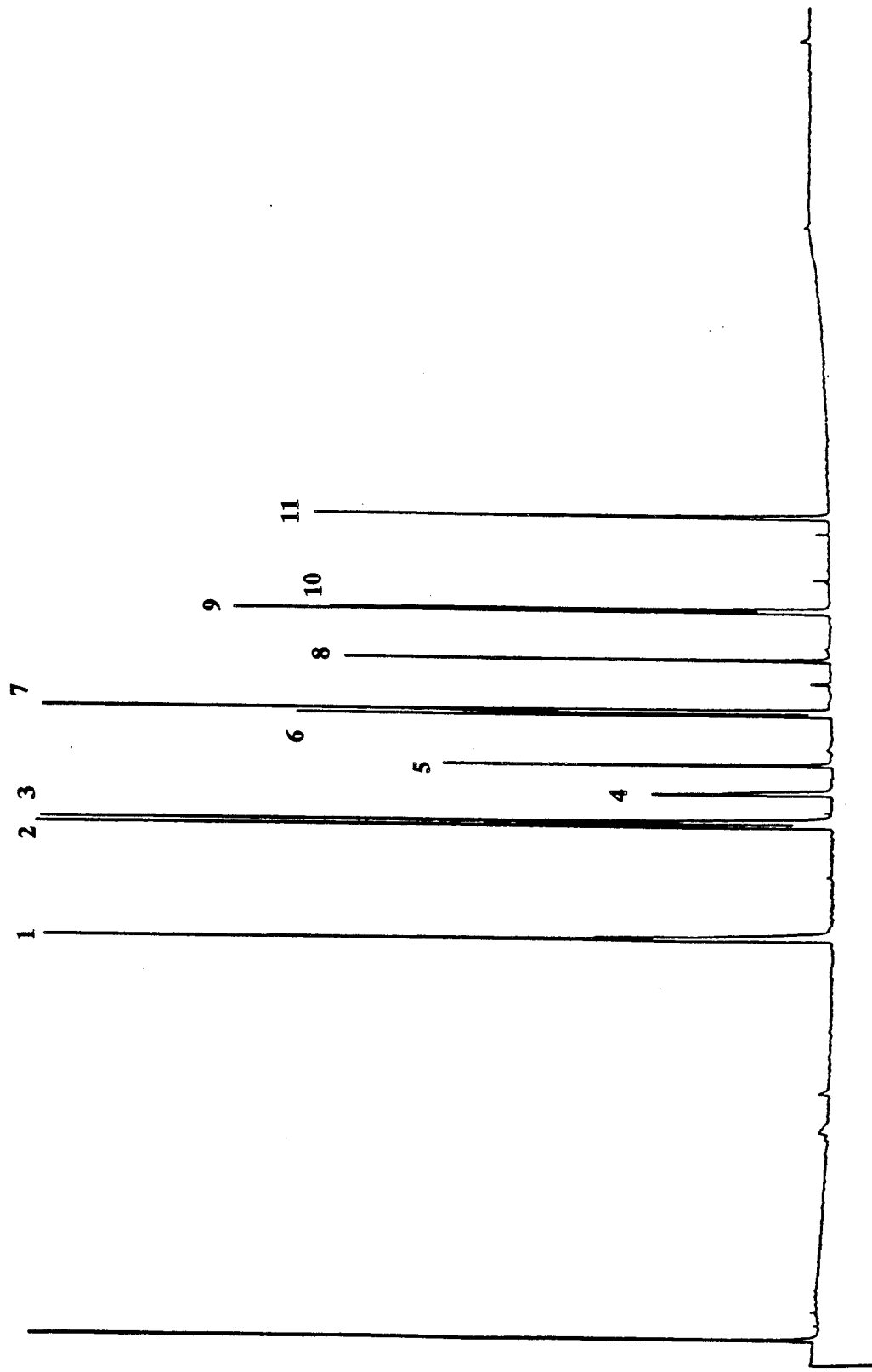
FIG. 4 illustrates a FIG. wherein a fatty acid methyl ester mixture was separated using a stationary phase made in accordance with yet another embodiment of the present invention.

FIG. 4 shows a gas FIG. of the separation of various fatty acid methyl esters by the new phase of Example 4. The FIG. shows that this polymer of the present invention provides an excellent separation of a hard-to-separate mixture. In FIG. 4, the peak identifications are as follows: (1) methyl hexadecanoate, (2) methyl 8-hexadecenoate, (3) methyl 9-octadecenoate, (4) methyl octadecanoate, (5) methyl 9,12,15-octadecatrienoate, (6) methyl nonadecanoate, (7) methyl 10-ercosenoate, (8) methyl ercosanoate, (9) methyl heneicosanoate, (10) methyl 11-docosenoate, (11) methyl docosanoate, and (12) methyl 12-tetracosenoate.

Figure 5:
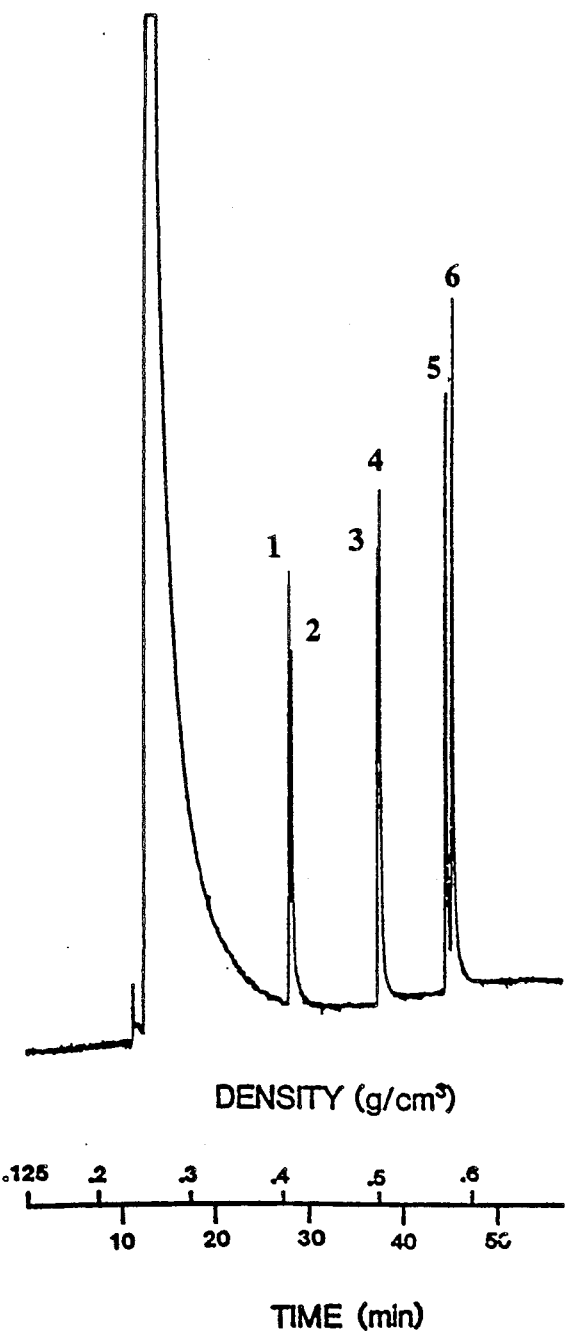
FIG. 5 illustrates a supercritical fluid FIG. wherein natural cholesterol type materials were separated on a stationary phase made in accordance with a different embodiment of the present invention.

The supercritical fluid chromatography (SFC) column (similar to Example 10) was chromatographically tested on a Lee Scientific Model supercritical fluid chromatograph. The column was 12.0 m×50 μm i.d. fused silica, 50% cyanopropyl polymethylhydrosiloxane-deactivated (250° C./10hr) and coated with a 0.25 micrometer film of a 45% polyethyl ether polysiloxane of Example 4. SFC conditions were supercritical carbon dioxide at 110° C.; 2.0 cm s$^{-1}$; mobile phase density held isoconfertic (constant density) for 12 min. at 0.125 g cm$^{-3}$, then programmed linearly at 0.01 g cm$^{-3}$ m$^{-3}$ to 0.6 g cm$^{-3}$; split injection flame ionization detection; 4×10$^{-12}$ amps full-scale response. The chromatogram of FIG. 5 shows the remarkable separation of isomeric pairs of mono-, di- and trihydroxyandrostane steroids. The isomer pairs are indicated by numerals in the peak identifications in the FIG. of FIG. 5 and are structurally identified by the same numerals in Table II which follows:

TABLE II

Structures in FIG. 5.

1. 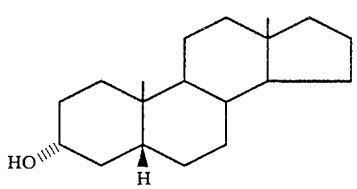

TABLE II-continued

Structures in FIG. 5.

2. 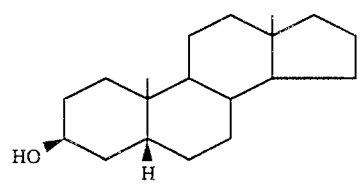

3. 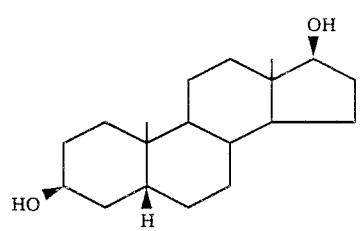

4. 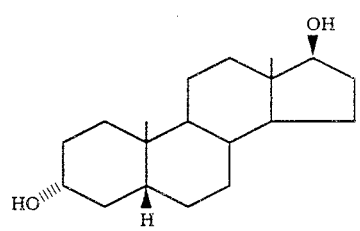

5. 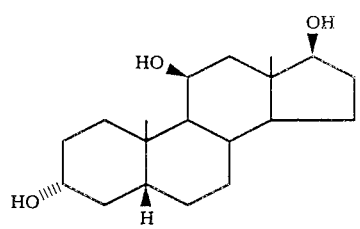

6. 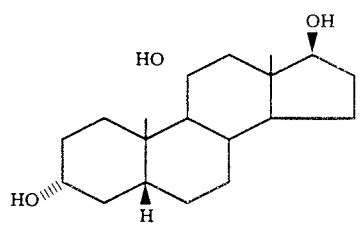

FIG. 5 shows how functional this embodiment of the invention is in separating isomeric pairs of relatively complex organic molecules utilizing oliogethylene oxide-substituted polysiloxanes.

From the foregoing, it will be appreciated that the polymers of the present invention provide stationary phases which are superior to the PEG phases in that they provide similiar separations of many organic mixtures, but at both lower (down to 20° C.) and higher operating temperatures (up to 280° C.). Further, the polymers of the present invention are suitable for use as stationary phases in SFC. In addition, obligosiloxanes containing Si-H functions as well as the compounds of Formula 2 can be used to prepare oligoethylene oxide-containing silica particles for LC use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A compound of formula

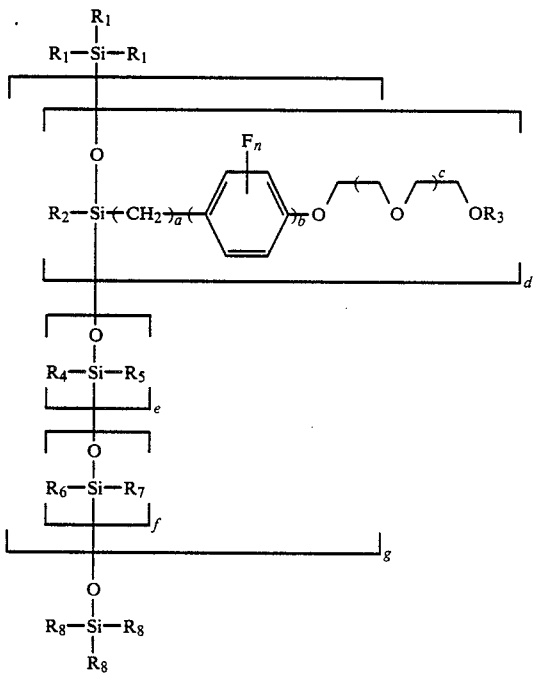

wherein;
a is an integer from 0 to about 14; b is an integer of 1 or 2; c is an integer from 0 to about 10; d is an integer from 1 to about 100; e is an integer from 0 to about 100. f is an integer from 0 to about 12; and g is an integer from 1 to about 50;

$R_1$ and $R_8$ are selected from the group consisting of lower alkyl, lower alkenyl, lowerhaloalkyl and phenyl;

$R_3$ is hydrogen, alkyl of 1-22 carbon atoms; fluorinated alkyl of 1-22 carbon atoms; aryl selected from the group consisting of phenyl, naphthyl, biphenyl, pyridyl, furyl, thienyl and pyrryl and the lower alkyl, lower alkoxy, cyano, nitro, fluoro, chloro, bromo, lower alkylsulfonyl, lower alkyl carboxyl, lower alkylamindo, lower dialkylamino and lower perhaloalkyl substituents thereof; or lower aralkyl;

$R_2$, $R_4$, $R_5$ and $R_6$ are members selected from the group consisting of hydrogen, lower alkyl, phenyl, phenyl substituted loweralkyl, loweralkyl substituted phenyl, lower alkoxy substituted phenyl and halosubstituted phenyl;

$R_7$ is a member selected from the group consisting of alkyl of 1 to 12 carbon atoms, alkenyl of 2 to 8 carbon atoms, phenyl substituted loweralkyl and loweralkyl substituted phenyl;

F is hydrogen, alkyl of 1 to 10 carbon atoms, fluorinated alkyl of 1 to 10 carbon atoms, alkoxy of 1 to 10 carbon atoms, phenyl, thienyl, furyl, pyridyl, pyrryl, nitro, cyano, chloro, bromo, fluoro, or $-(OCH_2CH_2)_m-OR_9$ wherein m and n are integers of 1 to 4 and $R_9$ is methyl or ethyl.

2. A compound as defined in claim 1 wherein a=3, b=1 and c=1 or 2.

3. A compound as defined in claim 1 wherein d=100 and e=0 to about 100.

4. A compound as defined in claim 1 wherein f=0 to about 3% of the total of d and e.

5. A compound as defined in claim 1 wherein g is an integer from 2 to about 50.

6. A compound as defined in claim 1 wherein $R_1$ and $R_8$ are all methyl (—$CH_3$).

7. A compound as defined in claim 1 wherein $R_3$ is methyl (—($CH_3$)) or ethyl (—$CH_2CH_3$).

8. A compound as defined in claim 1 wherein $R_2$, $R_4$, $R_5$ and $R_6$ are all methyl (—$CH_3$).

9. A compound as defined in claim 1 wherein $R_7$ is octyl (—$C_8H_{17}$).

10. A compound as defined in claim 1 wherein F is hydrogen.

11. A compound as defined in claim 1 wherein F is methoxy (—$OCH_3$).

12. A compound as defined in claim 1 wherein a=3, b=1, c=1, d=97, e=0, f=about 3, g=about 4, $R_1$ and $R_8$=methyl, $R_2$, $R_3$, $R_4$, $R_5$ and $R_6$ =methyl, $R_7$ =any combination of octyl and ethyl and F=H.

13. A compound as defined in claim 1 wherein a=3, b=1, c=2, d=50, e=50, f=about 3, g=about 4, $R_1$ and $R_8$=methyl, $R_2$, $R_3$, $R_5$ and $R_6$ methyl, $R_7$=any combination of octyl and ethyl, F=methoxy and n=1.

14. A compound as defined in claim 1 wherein a=0, b=1, c=2, d=100, e=0, f=about 3, g=3.5, $R_1$ and $R_8$=methyl, $R_2$, $R_3$, $R_4$, $R_5$ and $R_6$=methyl, $R_7$=octyl and F=H.

15. A compound as defined in claim 1 wherein a=3, b—1, c=1, d=6, e=6, f=0, g=about 1, F=hydrogen, $R_1$ and $R_8$=methyl, $R_2$ and $R_4$=methyl, $R_3$=ethyl, $R_5$=hydrogen, and $R_6$ and $R_7$ are not present since f=0.

* * * * *